US005731301A

United States Patent [19]

Michejda et al.

[11] Patent Number: 5,731,301
[45] Date of Patent: Mar. 24, 1998

[54] BISTRIAZENES AS CHEMOTHERAPEUTIC AGENTS

[75] Inventors: Christopher J. Michejda, North Potomac; Jeffrey J. Blumenstein, Germantown, both of Md.

[73] Assignee: The United States of America as represented by the Department of Health and Human Services, Washington, D.C.

[21] Appl. No.: 455,704

[22] Filed: May 31, 1995

Related U.S. Application Data

[62] Division of Ser. No. 82,902, Jun. 28, 1993, which is a continuation of Ser. No. 527,915, May 24, 1990, abandoned.

[51] Int. Cl.$^6$ .................................................. A61K 31/655
[52] U.S. Cl. ........................ 514/151; 534/550; 534/551; 534/552; 534/553; 534/554
[58] Field of Search ................. 514/151; 534/550–554

[56] References Cited

U.S. PATENT DOCUMENTS

| | | | |
|---|---|---|---|
| 3,138,521 | 6/1964 | Jelinek et al. | 534/550 X |
| 3,555,004 | 1/1971 | Mueller et al. | 534/550 X |
| 4,923,970 | 5/1990 | Michejda et al. | 534/550 |

FOREIGN PATENT DOCUMENTS

| | | | |
|---|---|---|---|
| 736959 | 2/1970 | Belgium | 534/550 |
| 3426644 | 2/1986 | Germany | 534/550 |

OTHER PUBLICATIONS

Clarke et al. (1955) Proc. Soc. Exp. Biol. Med. 90:484–88.
R.L. Comis, (1976) Cancer Treatment Reports 60:165–176.
Fiebig et al. (1987) European Journal of Cancer and Clinical Oncology 23:937–948.
Fiebig et al. (1989) Strahlenther. Onkol. 165:522–524.
B.T. Hill, (1987) Cancer Treatment Reviews 14:197–202.
Scalabrino et al. (1981) in Klein et al., eds., Advances in Cancer Research, vol. 35, Academic Press, N.Y., pp. 151–267.
Scalabrino et al. (1982) in Klein et al., eds., Advances in Cancer Research, vol. 36, Academic Press, N.Y., pp. 1–103.
A.E. Pegg, (1988) Cancer Research 48:759–774.
Randall et al. (1984) Journal Chem. Society Perkin Trans. II:251–253.
Schmiedekamp et al. (1988) Journal of Organic Chemistry 53:3433–3436.
Sieh et al. (1981) Journal of the American Chemical Society 103:442–445.
Smith et al. (1984) Journal of the American Chemical Society 106:1056–1059.
Smith et al. (1986) Journal of the American Chemical Society 108:3726–3730.
Smith et al. (1988) The Journal of Organic Chemistry 53:1467–1471.
Smith et al. (1986) The Journal of Organic Chemistry 51:3751–3757.
Smith et al. (1990) to be submitted J. Med. Chem.
Smith et al. (1989) The Journal of Organic Chemistry 54:1036–1042.
Vaughan et al. (1984) Journal of Medicinal Chemistry 27:357–363.
J.D. Watson, (1987) Molecular Biology of the Gene, The Benjamin Cummings Pub. Co., Inc., Menlo Park, CA, pp. 346–347.
Pochinok et al. I, Chemical Abstracts, vol. 54, No. 13034i (1960).
Pochinok et al. II, Chemical Abstracts, vol. 86, No. 188927K (1977).
Pochinok et al. III, Chemical Abstracts, vol. 102, No. 61876m (1985).
Vilenskii et al., Chemical Abstracts. vol. 67, No. 29572b (1967).
Pochinok et al. (1977) Ukr. Khim. Zh. (Russ. Ed.) 43(2):180–183 (Russ.).
Grant & Hackh's Chemical Dict. (1987) R. Grant et al. eds., McGraw-Hill Book Co., N.Y., pp. 49, 53, 177, 282, 461, 558.
Koepke et al. (1990) Chemical Research In Toxicology 3:17–20.
Sieh et al. (1980) J. Am. Chem. Soc. 102:3883.
Pochinok et al. I, Ukrain. Khim. Zhur. 25, 774–80 (1959).
English translation of Pochinok et al., *Ukrain. Khim. Zhur.*, 25, 774–80 (1959).

*Primary Examiner*—Fiona T. Powers
*Attorney, Agent, or Firm*—Spencer & Frank

[57] ABSTRACT

The present invention is directed to bistriazene compounds, pharmaceutical compositions containing effective anti-cancer amounts of these compounds, a method for treating cancer comprising administering to affected subjects an anti-cancer effective amount of a bistriazene compound, and the use of bistriazene compounds as crosslinking reagents applicable to the synthesis and manipulation of polymeric macromolecules.

14 Claims, 6 Drawing Sheets

| Lane | Compound | Concentration in mM |
|---|---|---|
| 1 | Control | — |
| 2 | Dimethyltriazene | 5.0 |
| 3 | " | 0.5 |
| 4 | " | 0.05 |
| 5 | 1,2-Bis(methyltriazeno)ethane | 5.0 |
| 6 | " | 0.5 |
| 7 | " | 0.05 |
| 8 | 1,4-Bis(methyltriazeno)-trans-2-butene | 5.0 |
| 9 | " | 0.5 |
| 10 | " | 0.05 |
| 11 | 1,6-Bis(methyltriazeno)hexane | 5.0 |
| 12 | " | 0.5 |
| 13 | " | 0.05 |
| 14 | α,α'-Bis(methyltriazeno)-p-xylene | 5.0 |
| 15 | " | 0.5 |
| 16 | " | 0.05 |

BISTRIAZENES AS CHEMOTHERAPEUTIC AGENTS

This application is a divisional of application Ser. No. 08/082,902, filed Jun. 28, 1993, now pending, which is a continuation of application Ser. No. 07/527,915, filed May 24, 1990, now abandoned.

BACKGROUND OF THE INVENTION

1. Field of the Invention

The present invention relates to the use of bistriazene compounds as chemotherapeutic agents useful in the treatment of various cancers. As such, these compounds find wide utility in both human and veterinary medicine. The invention also relates to the use of these compounds as crosslinking reagents useful in a wide variety of laboratory and chemical applications involving the synthesis and manipulation of polymeric macromolecules.

2. Description of Related Art

A number of chemotherapeutic agents exist which act as alkylating agents capable of forming covalent linkages with a variety of substances, including phosphate groups in DNA. Alkylation of bases in DNA often leads to gene miscoding, serious damage to the DNA molecule, and/or major disruption in nucleic acid function, and results in the inhibition of a wide range of other cellular functions. These agents act by forming lethal crosslinks in nucleic acid molecules, and can often shrink tumors in a matter of days after intravenous administration. Among these compounds are 2-chloroethyl-nitrosoureas such as bis(2-chloroethyl)nitrosourea (BCNU), mitomycin, cyclophosphamide (cytoxan), and ifosphamide. These agents are themselves potentially mutagenic, teratogenic, and carcinogenic, and their anti-neoplastic activity is exerted throughout the cell cycle, i.e., toxicity is cell cycle independent.

Vaughan et al. (1984) *Jour. Med. Chem.* 27:357–63 have reported the formation of a certain bistriazene as a by-product in the preparation of other triazenes. This bistriazene is chemically and structurally different from those of the present invention, and was not tested for antitumor activity. Furthermore, this bistriazene differs from those of the present invention in that it would require two-fold metabolic activation to release the same alkylating moiety, and is susceptible to hydrolysis, thereby releasing monotriazenes.

The use of the bistriazene compounds of the instant invention as chemotherapeutic and crosslinking agents has yet to be reported.

SUMMARY OF THE INVENTION

The bistriazene compounds of the present invention are novel alkylating agents which are structurally similar to polyamines such as spermine and spermidine, which interact with DNA. Most currently employed chemotherapeutic alkylating agents interact covalently or noncovalently with the target DNA, after which a crosslinking reaction may occur. The bistriazene compounds of the present invention differ from any known chemotherapeutic agents in that their chemical structure allows them to interact with the DNA molecule while maintaining their chemical integrity. This interaction depends on the formation of multiple hydrogen bonds with the DNA, and in this manner they appear to mimic natural polyamines which normally interact with DNA. In fact, it is possible that due to the structural similarity of the bistriazenes to some of the polyamines, the bistriazenes may occupy the same sites in DNA as the polyamines themselves. Subsequent to this binding, the bistriazenes decompose on the surface of the DNA, releasing the "Linker" in the form of a bisdiazonium ion. This highly reactive substance covalently interacts with the DNA, causing multiple double strand breaks and interstrand crosslinks. As the bisdiazonium ion can be made to vary in its properties by structural modification of the Linker in the bistriazene molecule, the reactivity of the entire molecule can be modulated by appropriate chemical modification. Thus, it appears that bistriazenes may interact with DNA in a polyamine-like fashion, subsequently breaking down to form crosslinking agents which result in the formation of crosslinks lethal to cells. The use of the bistriazene compounds of the present invention as chemotherapeutic drugs therefore confers great specificity of drug interaction with DNA, and because the reactive diazonium ions are formed on the surface of the DNA, delivers a much higher effective dose of the ultimate cytotoxic agent per molecule of administered compound than for simple monodentate drugs. This feature achieves the advantage that the dosage of such bistriazene-based drugs administered will be low in comparison to that of other conventional chemotherapeutic alkylating agents. The combination of specificity and low effective dose portends bistriazene-based anti-cancer drugs with much lower systemic toxicities than those currently in use.

Thus, the bistriazene compounds of the present invention represent an entirely novel class of bidentate, chemotherapeutic alkylating agents with greater specificity and lower toxicicity as compared to present treatments.

Accordingly, it is an object of the present invention to provide a method for treating cancer in a mammal, including humans, which comprises administering to the subject an anti-cancer effective amount of a bistriazene compound such as bis(methyltriazeno)-p-xylene, bis(methyltriazeno)-2-butene, bis(methyltriazeno)ethane, and other bistriazene derivatives.

Another object of the present invention is to provide a method for treating cancer in a mammal, including humans, which comprises administering to the subject an anti-cancer effective amount of a bistriazene compound and an anti-cancer effective amount of a an alkylating agent such as chlorambucil, melphalan, uracil mustard NF, cyclophosphamide, mechlorethamine hydrochloride, carmustine (BCNU), lomustine, dacarbazine (DTIC), thiotepa NF, and busulfan, or combinations of these latter compounds.

A further object of the present invention is to provide a pharmaceutical composition comprising an anti-cancer effective amount of a bistriazene compound.

Yet a further object of the present invention is to provide a pharmaceutical composition comprising an anti-cancer effective amount of a bistriazene compound or an anti-cancer effective amount of bistriazene compound and an anti-cancer effective amount of an alkylating agent such as chlorambucil, melphalan, uracil mustard NF, cyclophosphamide, mechlorethamine hydrochloride, carmustine (BCNU), lomustine, dacarbazine (DTIC), thiotepa NF, and busulfan, or combinations of these latter compounds.

These objects and others are accomplished in accordance with the present invention by administering an anti-cancer effective amount of a pharmaceutical composition containing a bistriazene compound or a physiologically acceptable salt thereof. Representative bistriazene compounds useful in treating cancer include bis(methyltriazeno)-p-xylene, bis (methyltriazeno)-2-butene, bis(methyltriazeno) ethane, and other bistriazene derivatives which are anti-cancer agents, such as the following:

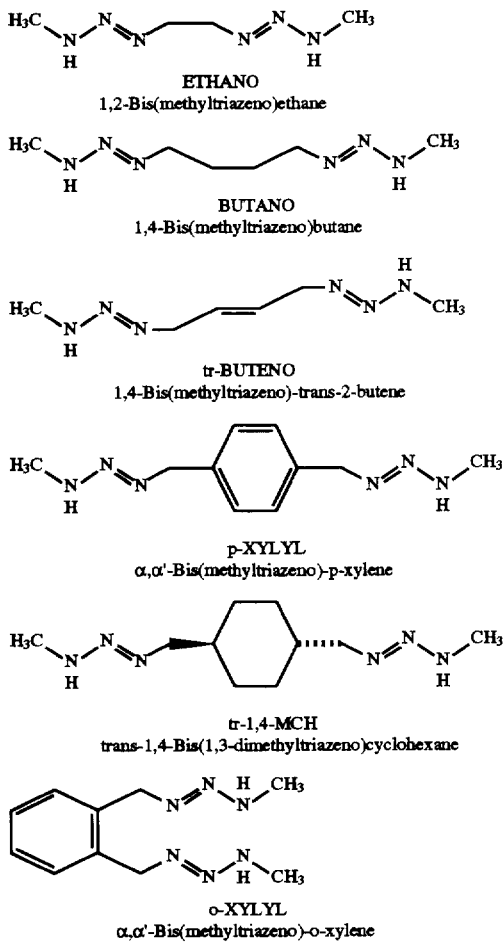

The compounds of the present invention can be used for the treatment of human and animal cancers.

In addition to the use of bistriazene compounds for the therapeutic treatment of neoplastic disease, the use of these compounds as laboratory reagents is also envisioned as another object of the present invention. In the laboratory manipulation of macromolecules such as DNA and proteins, reagents are often employed which interact with the molecule of interest such that the molecule is:

1) Cut in a specific region;
2) Blocked from being enzymatically cut in a specific region;
3) Bound to another molecule with which it is loosely associated;
4) Bound to a matrix such as nitrocellulose or nylon to facilitate handling and probing;
5) Bound to a matrix such as a chromatography support as a ligand for affinity chromatography; or
6) Conjugated to unrelated macromolecules (e.g., toxins to antibodies, antibodies to enzymes, small molecules to oligonucleotide DNA probes, etc.). Bistriazenes can be adapted for use in these and other laboratory manipulations of macromolecules.

If the bistriazene is modified such that the substituent groups afford a high degree of sequence recognition, then upon alkylation at a labile site, breakage of the DNA or protein backbone may occur (#1 above). Alternatively, alkylation at a stable site may block enzymatic digestion such as restriction enzyme digestion of DNA or protease digestion of proteins (#2 above).

Multifunctional chemical crosslinking agents are presently widely used in applications #3, #5, and #6 cited above. The use of bistriazene compounds in such applications is another object of the present invention.

It is further envisioned that bistriazene compounds will be employed as highly active chemical crosslinking agents useful in immobilizing molecules such as RNA, DNA or proteins on nitrocellulose, nylon, or other similar membranes (application #4, above), thereby facilitating the handling and probing of these biopolymers on such membrane supports.

Yet another object of the present invention is to employ bistriazenes as crosslinking agents in the formation of chemical polymers from their monomeric constituents.

The bistriazene compounds of the present invention may be employed as chemical crosslinking agents in a manner similar to that of other well known crosslinking agents, as would be apparent to one of ordinary skill in the art.

Further scope of the applicability of the present invention will become apparent from detailed description and drawings provided below. However, it should be understood that the detailed description and specific examples, while indicating preferred embodiments of the invention are given by way of illustration only since various changes and modifications within the spirit and scope of the invention will become apparent to those skilled in the art from this detailed description.

BRIEF DESCRIPTION OF THE DRAWINGS

In FIGS. 1–4, the abbreviations of the cell lines represent the following:

CXF, Colon Cancer Xenograft; GXF, Gastric; LXF, Lung: A adeno, L large cell, E epidermoid cell, S small cell; MAXF, Mammary Cancer Xenograft; MEXF Melanoma; PXF, Pleuramesothelioma; SXF, Sarcoma; TXF, Testicular; XF, miscellaneous Cancer Xenograft.

Figure 5:
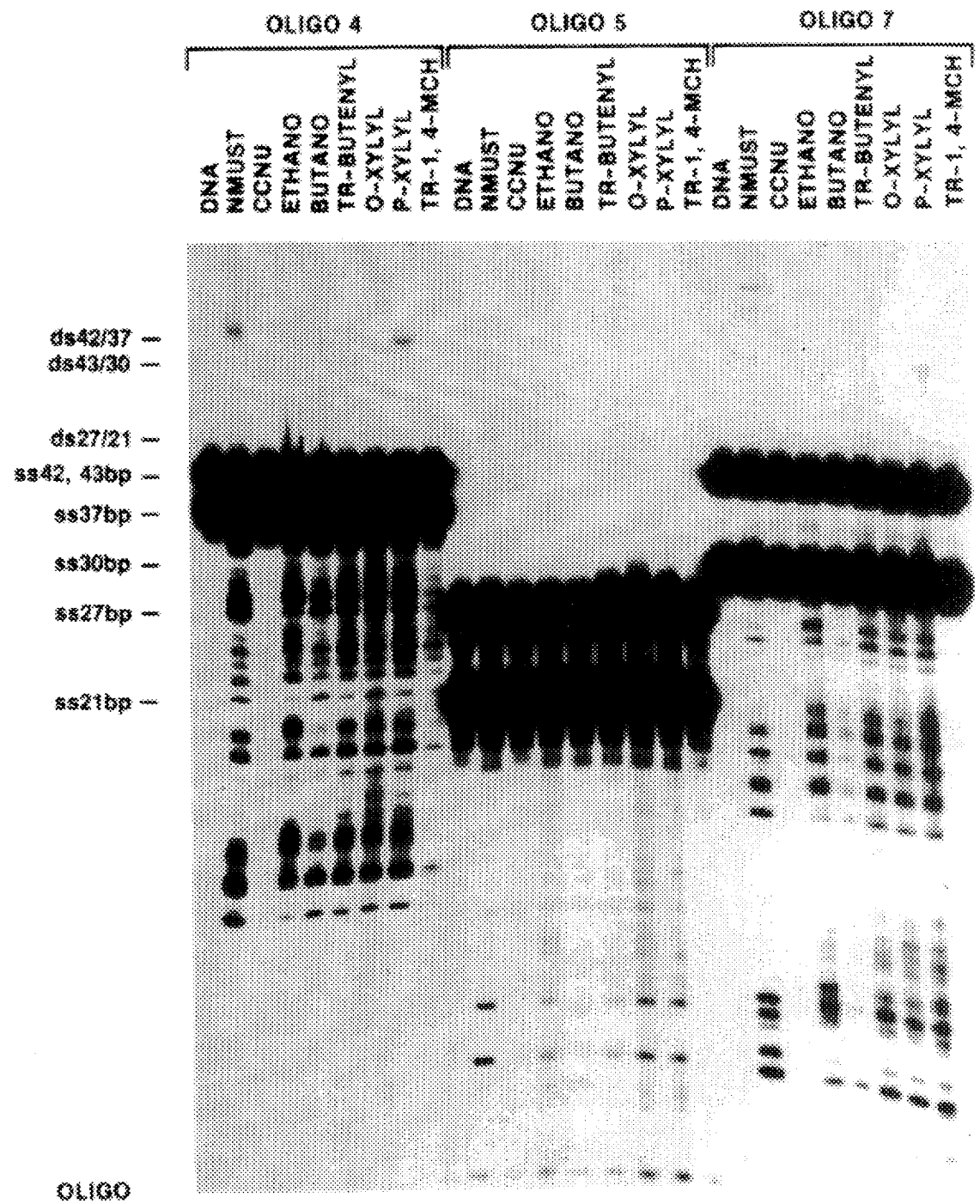

FIG. 5 shows the results of the oligonucleotide crosslinking assay.

Figure 6:
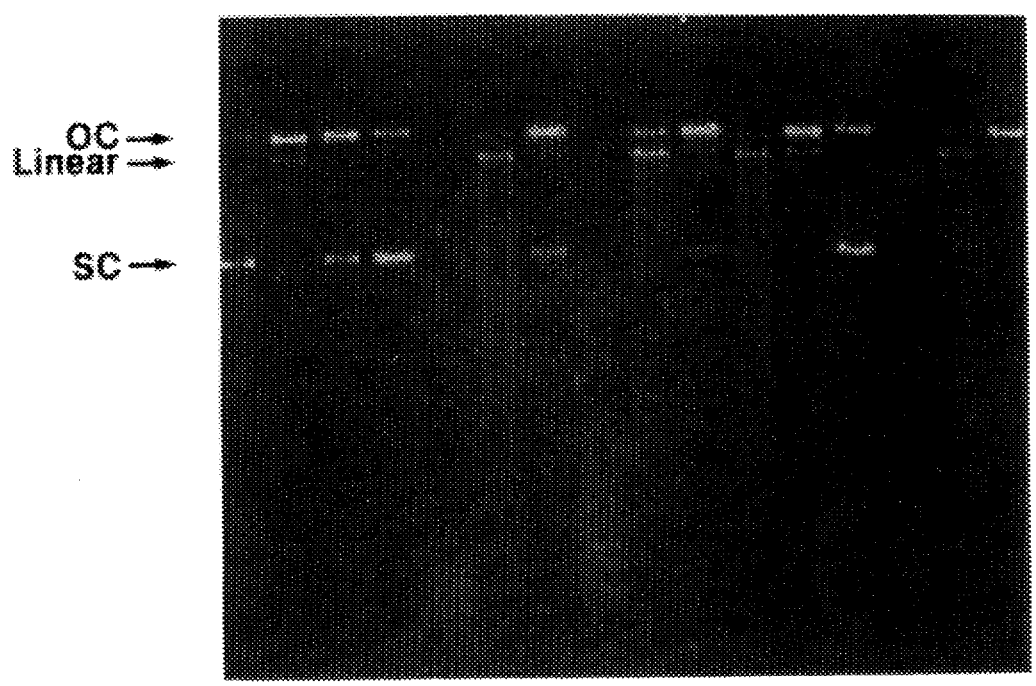

FIG. 6 shows the results of the supercoiled plasmid DNA assay.

DETAILED DESCRIPTION OF THE INVENTION

As those of ordinary skill in the art will recognize, the basic bistriazene structure contains a number of elements which can be modified to affect the desired use of these compounds. These elements are indicated in the following structure:

The "Linker" moiety is involved in the structural definition of the molecule and in crosslink formation. The Linker can be either an alkyl group, substituted alkyl (including, but not limited to, alkylamines, alkyl ethers and thioethers, haloalkyl, silanes, phosphines, alcohols, amines, etc.), of chain length 1–20, preferably 2–8. The Linker may also include aralkyl or substituted aralkyl (with modifications analogous to those for substituted alkyls), polycyclic aralkyl, heterocyclic aralkyl, and their substituted derivatives wherein the triazine moieties can be separated by 1–30 carbon atoms, preferably 4–12 carbon atoms.

With regard to the "End Group" (EG), this moiety is crucial in modulating the reactivity of bistriazenes. The EGs may be identical or independently selected from groups comprising alkyl groups, substituted alkyl (including, but not limited to, alkylamines, alkyl ethers and thioethers, haloalkyl, silanes, phosphines, alcohols, amines, etc.), of chain length 1–20, preferably 1–6. The EG may also include aralkyl or substituted aralkyl (with modifications analogous to those for substituted alkyls), polycyclic aralkyl, aryl groups and heterocyclic groups of 2–40 non-hydrogen atoms, containing 1–6 rings, including nucleic acid bases and oligonucleotides.

The final substituent on the triazene moiety, i.e., R or R', is perhaps the most fungible, and may be added following assembly of the basic triazene moiety by methods described for simple dialkyltriazenes (R. H. Smith, Jr., et al., *J. Org. Chem.*, 1986, 51, 3751; R. H. Smith, Jr., et al., *J. Org. Chemo*, 1988, 53, 1467; D. H. Sieh, et al., *J. Am. Chem. Soc.*, 1980, 102, 3883; R. H. Smith, Jr. and C. J. Michejda, *Synthesis*, 1983, 476). R or R' may be identical to EG or to one another, or may be independently selected from the groups comprising hydrogen, alkyl groups, substituted alkyl (including, but not limited to, alkylamines, alkyl ethers and thioethers, haloalkyl, silanes, phosphines, alcohols, amines, etc.) of chain length 1–20, preferably 1–6. R or R' may also include aralkyl or substituted aralkyl (with modifications analogous to those for substituted alkyls), polycyclic aralkyl, aryl groups, and heterocyclic groups of 2–40 non-hydrogen atoms, containing 1–6 rings. Additionally, R may be an acid derivative where the original acid includes, but is not limited to, carboxylic, sulfuric, sulfonic, phosphoric, phosphinic, arsenic, and selenic acids.

R may also include, in the examples cited above, compounds where R equals R', or R is linked to R' such that a cyclic bistriazene compound is formed. Cases where R equals R' may be expanded to include multivalent metals including, but not limited to, palladium, platinum, titanium, zirconium, silicon, selenium, magnesium, and copper. Several metal species such as cisplatin and titanocene dichloride are clinically active as antineoplastic agents, and the bistriazene moiety may serve as a bidentate ligand for these classes of compounds in order to generate compounds with multiple modes of cytotoxic action. If R is linked to R', polymeric compounds may result in addition to cyclic bistriazenes. The polymers produced would have unusual physical properties due to the hydrolytic instability of triazenes. It can be envisioned that this can be used to prepare polymers which could be implanted, and which would hydrolytically decompose to produce active cytotoxic agent in a time release manner. Similarly, it may be that the polymer would only provide a slowly dissolving matrix. This matrix may be used for structural applications, or to release an entrapped substance.

Furthermore, it should be noted that, while for simplicity, all modifications mentioned above have been discussed as being symmetrical, this need not be the case, and asymmetrical bistriazene molecules are encompassed among the compounds of the present invention.

SYNTHESIS OF BISTRIAZENES

The synthesis of bistriazenes is readily accomplished by the reactions shown below:

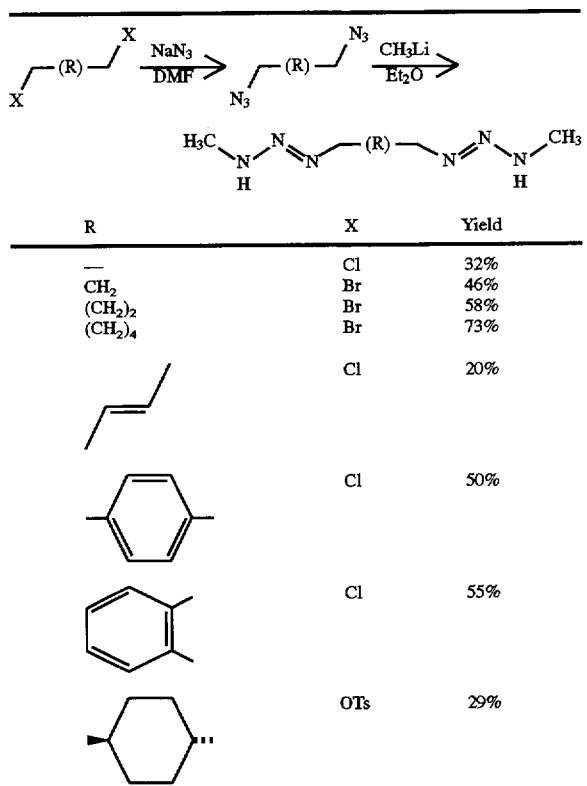

In general, bistriazenes are prepared by the reaction of 1,ω-diazidoalkanes with two equivalents of an alkyllithium. The diazidoalkanes are prepared from the corresponding dihaloalkanes and sodium azide in dimethylformamide solution. For example, the simplest bistriazene, 1,2-bis(methyltriazeno)ethane (BMTE), is prepared by the reaction of 1,2-diazidoethane with two equivalents of methyllithium.

In contrast to simple triazenes, bistriazenes are crystalline solids. X-ray crystal structure determination of BMTE reveals that the molecule adopts a conformation in the solid state which maximizes hydrogen bond interactions with its neighbors. In this regard, BMTE is remarkably similar to polyamines such as spermine, spermidine, and their phosphatidyl derivatives, which are known to bind strongly to DNA.

The synthesis and X-ray crystal structure of bistriazenes are described in Blumenstein et al., *Tetrahedron Letters*, submitted for publication, and Blumenstein et al., *Chemical Communications*, submitted for publication, respectively. The synthesis of particular bistriazenes is as follows:

EXAMPLE 1

Trans-1,4-bis(methyltriazenomethyl)cyclohexane

A flask is charged with 3.0 g (6.6 mmole) of trans-1,4-di(methyl 4-toluenesulfonate)cyclohexane, 1.08 g (16.6 mmole) of sodium azide, and 50 ml of dimethylformamide (DMF). The mixture is heated at 50° C. with stirring under argon for 2 days. The mixture is then diluted with 150 ml of water and extracted four times with 40 ml of petroleum ether. The combined organic layers are dried over $Na_2SO_4$, filtered, and evaporated to afford a pale yellow oil. The residual oil is dissolved in 100 ml of anhydrous ether and cooled to −20° C. under argon. A 1.5M solution of MeLi in ethyl ether (11 ml, 16.5 mmoles) is added to the solution over 0.5 hr. A white precipitate begins to form after a small amount of the MeLi has been added. The cooling bath is removed and the mixture is allowed to stir overnight. Excess MeLi is quenched by the careful addition of 30 ml of half-saturated $NH_4Cl$ with cooling of the solution. Vigorous gas evolution accompanies the addition of the first several ml of $NH_4Cl$, and the addition is carried out as quickly as possible. The aqueous layer is then rapidly separated, washed with 40 ml of water, dried over $Na_2SO_4$, filtered, and evaporated to afford a pale tan solid. The solid is recrystallized from ether/petroleum ether to yield 430 mg (29% yield) of a white solid, mp 72°–3° C. Mass spectra (FAB) Calc (M+H) 227.1984, Found 227.2017±0.0023.

EXAMPLE 2

1,4-Bis(methyltriazenomethyl)benzene

A flask is charged with 2.0 g (11.4 mmole) of 1,4-di(chloromethyl)benzene, 1.86 g (28.6 mmole) of sodium azide, and 50 ml of DMF. The mixture is heated at 50° C. with stirring under argon overnight. The mixture is worked up and treated with 20 ml of a 1.4M solution of MeLi (28 mmole) as described above. After workup, a yellow solid is obtained. Crystallization from ether/petroleum ether affords 1.26 g (50% yield) of a pale yellow solid, mp 90°–2° C. Mass spectra (FAB) Calc (M+H) 221.1514, Found 221.1558±0.0022

EXAMPLE 3

1,2-Bis(methyltriazenomethyl)benzene

A flask is charged with 7.96 g (45 mmole) of 1,2-di(chloromethyl)benzene, 7.39 g (114 mmole) of sodium azide, and 150 ml of DMF. The mixture is heated at 50° C. with stirring under argon overnight. The mixture is worked up, and in 300 ml of anhydrous ether, is treated with 90 ml of a 1.3M solution of MeLi (117 mmole) as described above. After workup, a yellow-orange oil is obtained. Kugelrohr distillation (110°–120° C., 0.5 mm) affords 5.40 g (55% yield) of a pale yellow oil which darkened and became a semi-solid upon standing. Mass spectra (FAB) Calc (M+H) 221.1514, Found 21.1513±0.0022.

EXAMPLE 4

1,4-Bis(methyltrizeno)butane

A flask is charged with 4.0 g (18.5 mmole) of 1,4-dibromobutane, 3.6 g (55 mmole) of sodium azide, and 50 ml of DMF. The mixture is heated at 50° C. with stirring under argon overnight. The mixture is worked up and treated with 45 ml of a 1.3M solution of MeLi (58 mmole) as described above. After 3 hr the reaction is worked up as described above, and a yellow solid is obtained. Crystallization from ether/petroleum ether affords 1.86 g (58% yield) of a white solid, mp 40°–2° C. Mass spectra (FAB) Calc (M+H) 173.1514, Found 173.1510±0.0017.

EXAMPLE 5

1,2-Bis(methyltriazeno)ethane

A flask is charged with 5.0 g (27 mmole) of 1,2-dibromoethane, 3.8 g (58 mmole) of sodium azide, and 50 ml of DMF. The mixture is heated at 50° C. with stirring under argon overnight. The mixture is worked up as described above, except that the azide solution is not evaporated down totally. When about 30 ml of solution remains the mixture is treated with 45 ml of a 1.3M solution of MeLi (58 mmole) as above. After 3 hr the reaction is worked up as described above, and a yellow solid is obtained. Crystallization from ether/petroleum ether affords 1.23 g (32% yield) of an off-white solid, mp 64°–6° C. Mass spectra (FAB) Calc (M+H) 145.1201, Found 145.1220±0.0015.

EXAMPLE 6

1,6-Bis(methyltriazeno)hexane

A flask is charged with 10.0 g (41 mmole) of 1,6-dibromohexane, 6.66 g (102 mmole) of sodium azide, and 100 ml of DMF. The mixture is heated at 50° C. with stirring under argon overnight. The mixture is worked up and as a solution in 400 ml of anhydrous ether, is treated with 77 ml of a 1.3M solution of MeLi (100 mmole) as described above. After 3 hr the reaction is worked up as described above, and a yellow solid is obtained. Crystallization from ether/petroleum ether affords 5.96 g (73% yield) of a white solid, mp 54°–5° C.

EXAMPLE 7

1,4-Bis(methyltriazeno)-trans-2-butene

A flask is charged with 12.5 g (100 mmole) of 1,4-dichloro-trans-2-butene, 14.3 g (220 mmole) of sodium azide, and 200 ml of DMF. The mixture is stirred under argon overnight, worked up, and as a solution in 400 ml of anhydrous ether, is treated with 130 ml of a 1.4M solution of MeLi (183 mmole) as described above. After 3 hr the reaction is worked up, and a yellow solid is obtained. Crystallization from ether/petroleum ether affords 3.34 g (20% yield) of a pale yellow solid, mp 71°–4° C. Mass spectra (FAB) Calc (M+H) 171.1358, Found 171.1397±0.0017.

EXAMPLE 8

1,6-Bis(methyltriazeno)propane

A flask is charged with 10.0 g (49.5 mmole) of 1,3-dibromopropane, 7.08 g (109 mmole) of sodium azide, and 100 ml of DMF. The mixture is stirred under argon overnight, worked up, and as a solution in 400 ml of anhydrous ether, is treated with 80 ml of a 1.4M solution of MeLi (112 mmole) as described above. After 3 hr the reaction is worked up as described above, and a yellow solid is obtained. Crystallization from ether/petroleum ether affords 3.61 g (46% yield) of a white solid, mp 55°–7° C. Mass spectra (FAB) Calc (M+H) 159.1358, Found 159.1360±0.0016.

BIOLOGICAL ACTIVITY

The bistriazene compounds of the present invention are useful in the treatment of a wide variety of cancers, as shown from the data below.

Clonogenic Assay. The response of a variety of human tumor cell lines to bistriazenes was determined via the clonogenic assay described in Fiebig et al. (1987) *European Journal of Cancer and Clinical Oncology* 23: 937–948.

Briefly, the assay system consists of a modified, two-layer soft agar culture system. The bottom layer consists of 1 ml of modified Dulbecco medium supplemented with L-glutamine, containing 10% fetal calf serum and 0.5% agar, in a 35 mm petri-dish. The upper layer contains 2–5×10⁵ viable human tumor cells suspended in a 1 ml volume, consisting of 0.3% agar, 30% fetal calf serum, and the medium. The drugs to be tested, contained in 1 ml of medium containing 30% fetal calf serum, are included in the upper layer. Control plates are identical, except for the omission of the drugs. The plates are incubated at 37° C. in a humidified atmosphere containing 7% carbon dioxide for varying periods (7–21 days). The time in culture is determined by the rate of colony formation in the control plates. At the end of the culture period, the number of colonies in the drug treated cultures is compared to the number of colonies in the control plates, after visualization of the live colonies by staining with tetrazolium chloride.

Three different bistriazenes were examined in the assay. In all cases, the End Group (EG) was methyl, while the Linker was varied:

Linker p-xyleleno,  —CH₂—C₆H₄-CH₂—trans-2-buteno, —CH₂CH=CHCH₂-ethano, —CH₂CH₂—

Each of these compounds was evaluated against a panel of human tumor cells, the identity of which is indicated in FIGS. 1–4. The tumors included those derived from colon cancer, three types of lung cancer, mammary cancer, ovarian cancer, two types of kidney cancer, a mesothelioma, a gastric cancer, and a sarcoma. These tumors represent some of the most important cancers for which current treatments are inadequate. For comparison, the assays of the various bistriazenes were compared to the response induced in the same tumors by DTIC, a drug employed in clinical practice.

Figure 1:
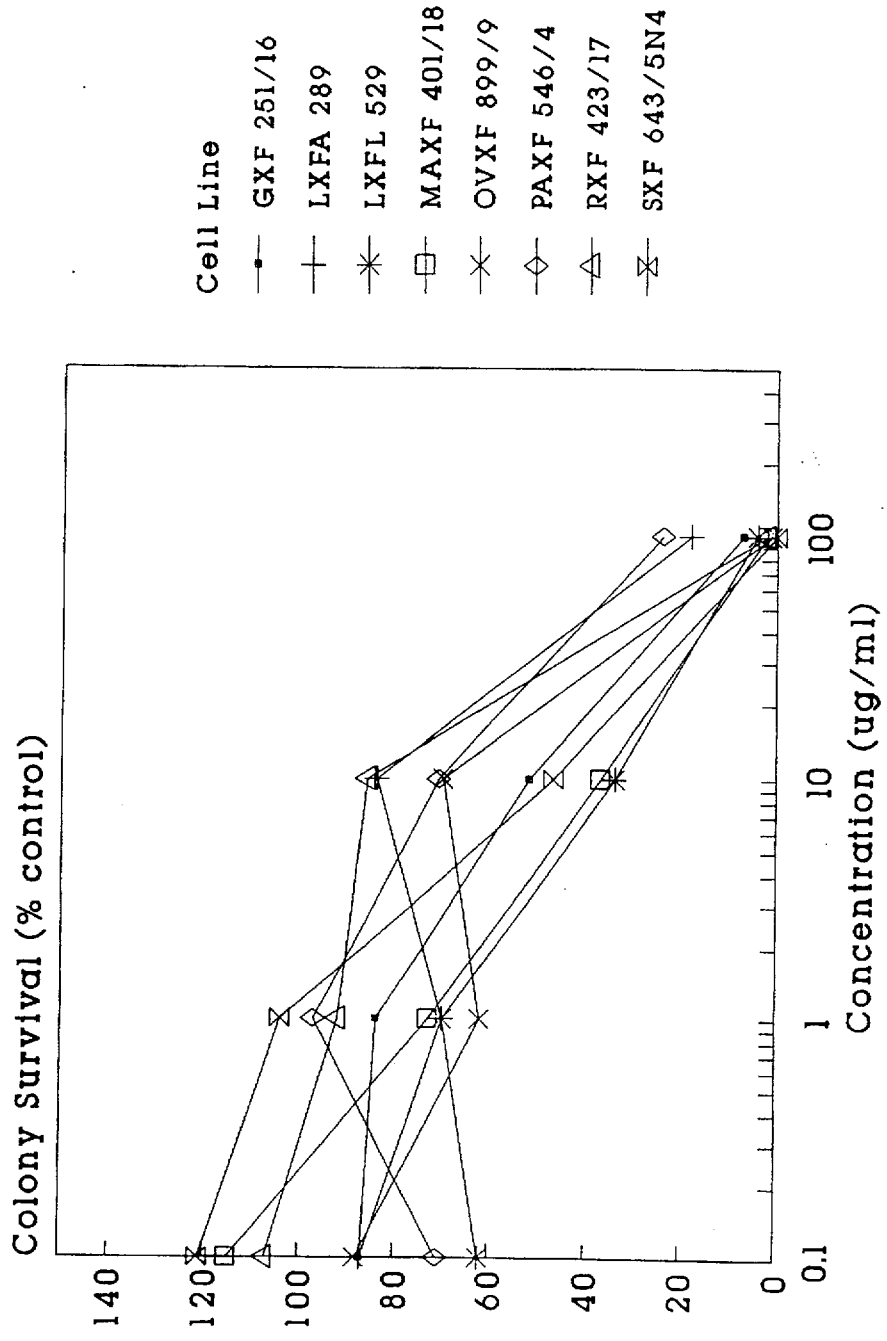
FIG. 1 shows the survival in vitro of several human tumor cell lines exposed to various concentrations of bis (methyltriazeno)-p-xylene.

FIG. 1 shows dose-response curves obtained in the in vitro clonogenic cytotoxicity assay against several human tumor cell lines employing bis(methyltriazeno)-p-xylene. At a dose of 100 ug/ml, this compound was highly toxic to all tumor cell lines. At a dose of 10 ug/ml, it exhibited toxicity against approximately half of the cell lines examined. Some activity was also evident at a dose of 1 ug/ml in about half the cell lines.

Figure 2:
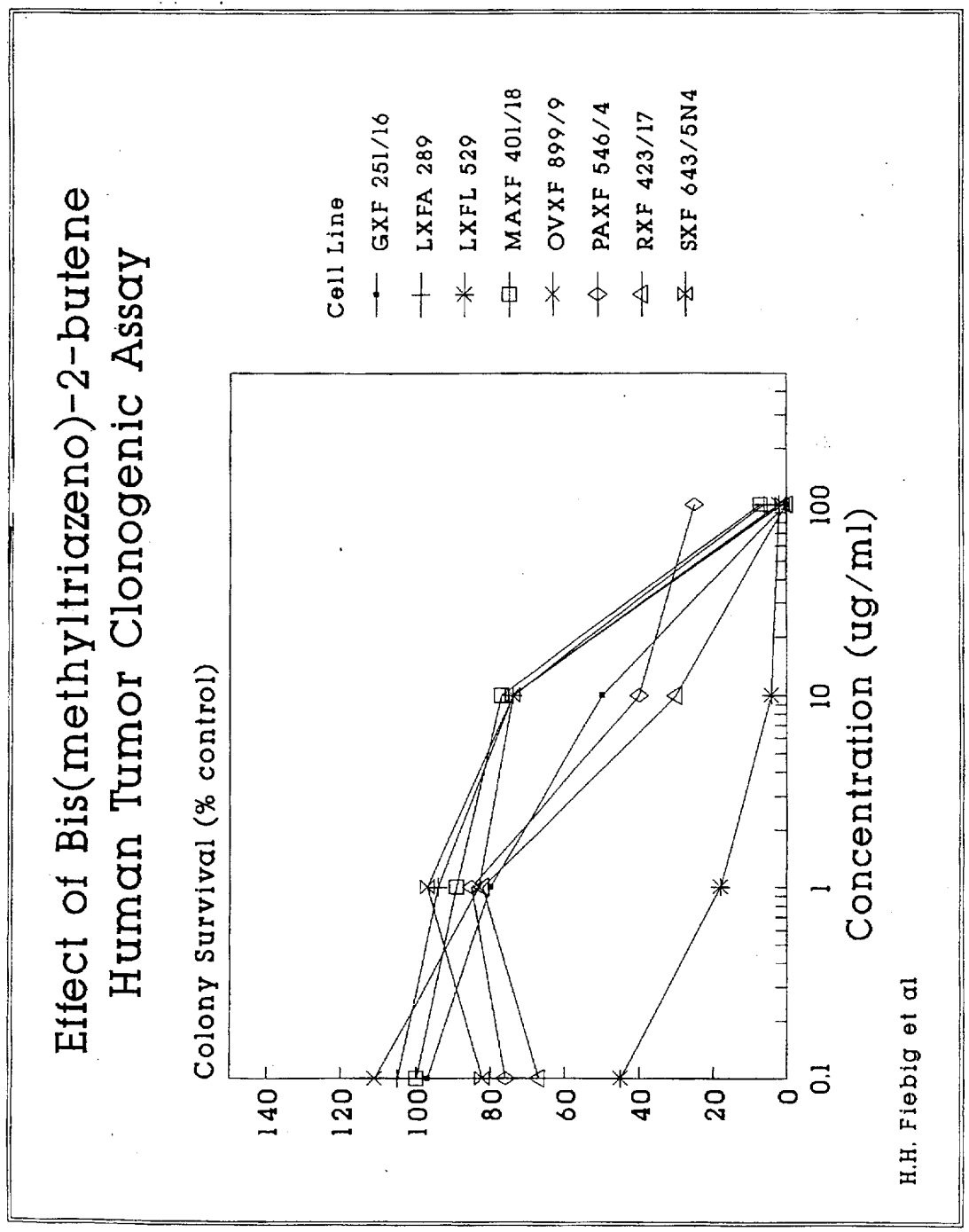
FIG. 2 shows the survival in vitro of several human tumor cell lines exposed to various concentrations of bis (methyltriazeno)-2-butene.

The data in FIG. 2 disclose the results obtained with 1,4-bis(methyltriazeno)-trans-2-butene. This drug exhibited potent cytotoxic activity against all the tumors tested at 100 ug/ml. This activity persisted at 10 ug/ml, especially for the large cell lung carcinoma LXFL529 and the renal cancer RXF423/17. At a dose of 1 ug/ml, there was still significant activity against the lung cancer. Thus, 1,4-bis (methyltriazeno)-trans-2-butene is a potently active compound, the cytotoxic activity of which is highly specific for certain types of cancers.

Figure 3:
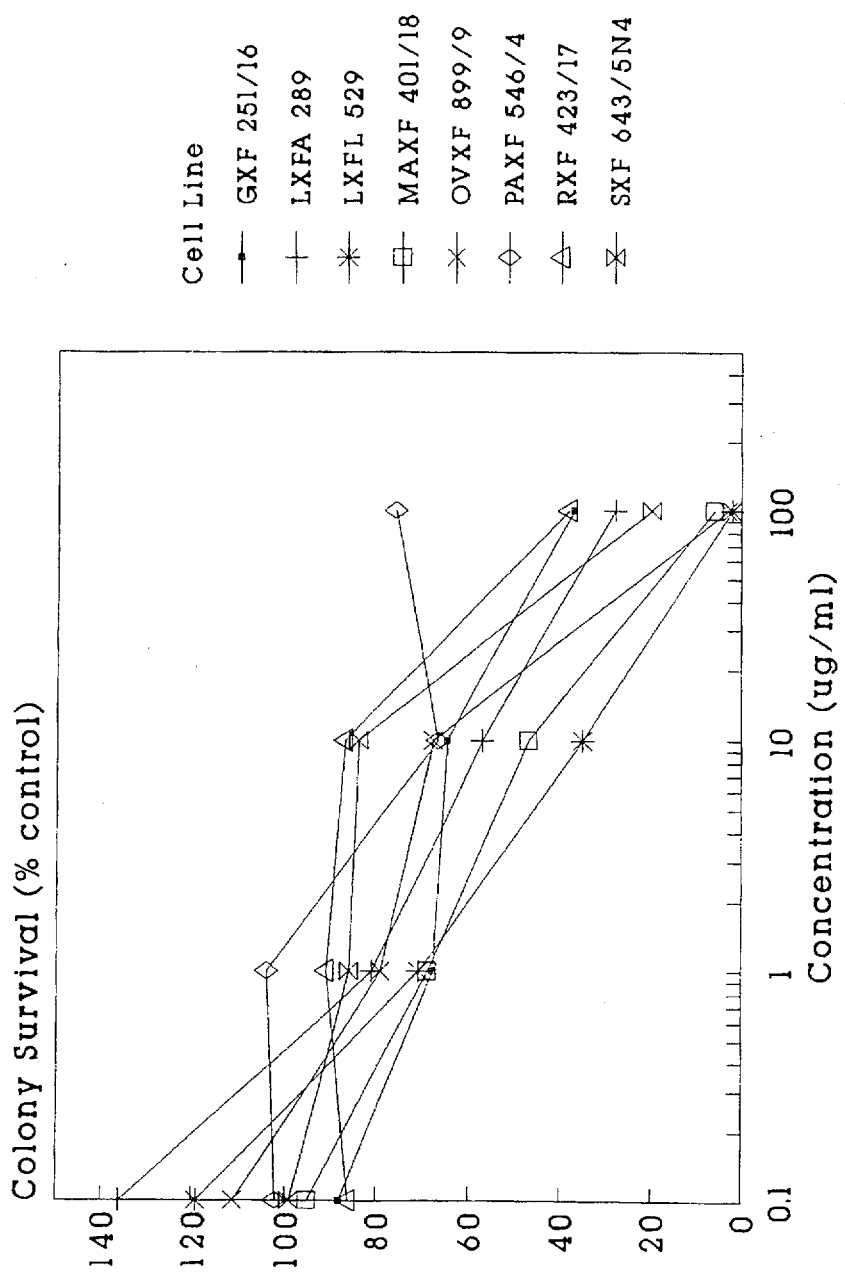
FIG. 3 shows the survival in vitro of several human tumor cell lines exposed to various concentration of his (methyltriazeno)ethane.

FIG. 3 discloses the results obtained with bis (methyltriazeno)ethane in the clonogenic assay. This compound was highly cytotoxic at 100 ug/ml to most of the tumor cell lines. Relatively little or no activity was observed, however, in the mesothelioma, the gastric carcinoma, or the renal cancer RXF 423/17. At 10 ug/ml, only marginal, but significant, activity was seen in the large cell lung cancer and in the mammary cancer.

Figure 4:
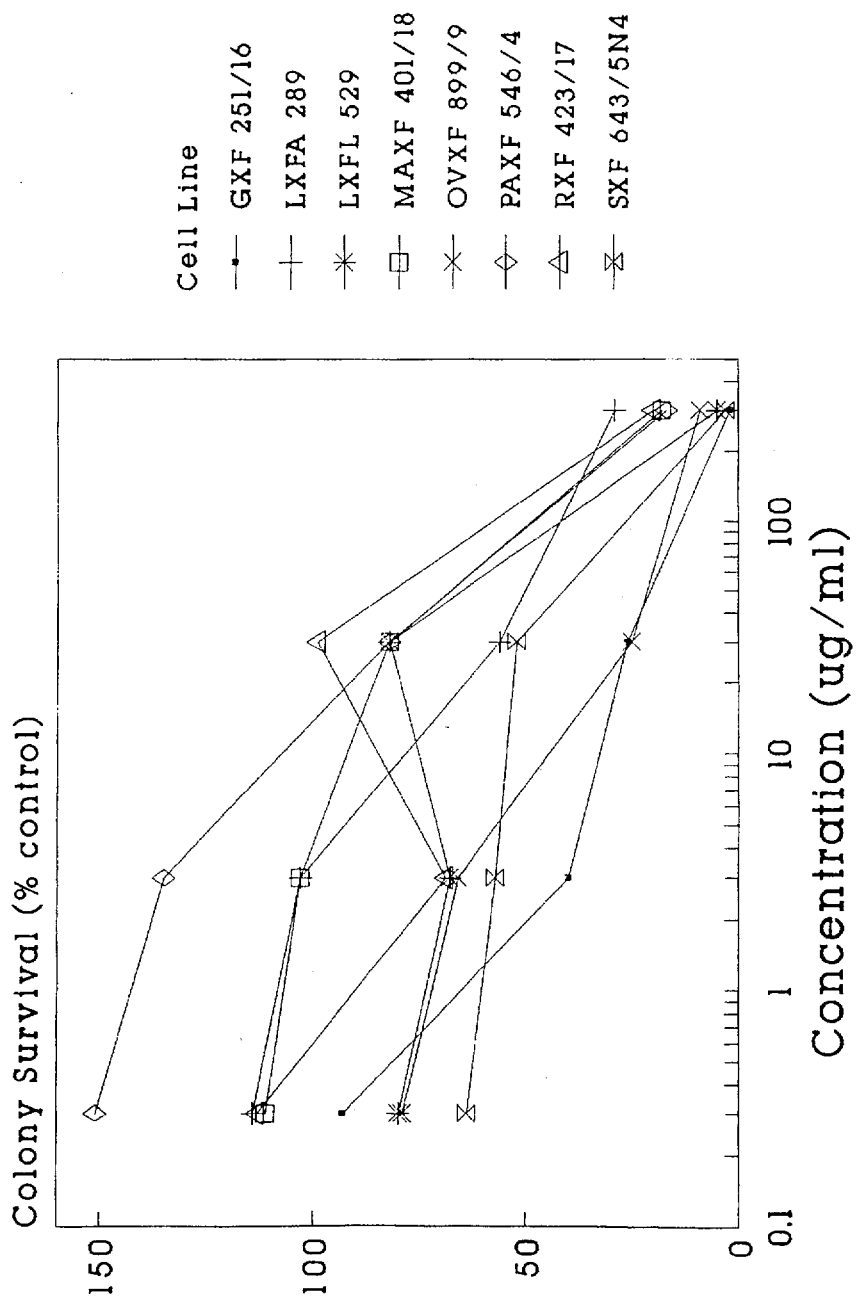
FIG. 4 shows the survival in vitro of several human tumor cell lines exposed to various concentrations of 5-(3,3-dimethyltriazeno) imidazole-4-carboxamide (DTIC).

For comparative purposes, the activity of DTIC (5-(3,3-dimethyltriazeno) imidazole-4-carboxamide) was tested in these cell lines. The results are shown in FIG. 4. DTIC is used clinically against metastatic melanoma, non-Hodgkins lymphoma, and soft-tissue sarcomas. At each point, the dose of DTIC was 3 times larger than that of the bistriazenes. Thus, at 300 ug/ml, DTIC was potently cytotoxic on all cell lines. At 30 ug/ml, it showed activity against the gastric carcinoma GXF251/16 and the ovarian cancer OVXF899/9. At 3 ug/ml, it exhibited marginal activity against the gastric cancer. Thus, all of the bistriazenes tested in this assay were at least as potent as DTIC. The bistriazene 1,4-bis (methyltriazeno)-trans-2-butene is highly potent against several tumors, especially the large cell lung carcinoma.

It may be concluded from these data that bistriazenes, as a class of compounds, are cytotoxic agents which exhibit considerable selectivity toward certain tumors. It is also clear from these data that the nature of the Linker is of paramount importance in modulating the activity and selectivity of cytotoxic action of these compounds. The clonogenic assay system facilitates rapid testing of the anti-tumor activities of newly sythesized bistriazenes containing systematically varied EG's and Linkers, in order to establish the chemical and biological characteristics which will result in additional useful drugs.

CHEMICAL ACTIVITY

Crosslinking of Oligonucleotides: The reaction of bistriazenes can afford interstrand crosslinks if the triazene decomposition produces alkydiazonium ions at each end of the Linker chain.

Bistriazenes react with varying efficiency with different oligonucleotides. Unsaturated bistriazenes such as p-xylyl and trans-butenyl produce stable crosslinked species in oligonucleotides. The amount of crosslinked species varies with the oligonucleotide sequence. The level of crosslinking is comprable to that seen with nitrogen mustard, and exceeds that observed with 1-(2-chloroethyl)-3-cyclohexyl-1-nitrosourea.

The crosslinking of oligonucleotides by bistriazenes was demonstrated in the following assay system:

A solution of 6.2 ng of ³²P-endlabeled oligonucleotide in 0.1M cacodylic acid buffer (0.1M NaCl, pH 7.4) was allowed to react with the desired compound dissolved in ⅒ volume DMSO. Final concentrations of the compounds in the oligonucleotide solution were 0.1 mM NMUST, 1.0 mM CCNU, or 10 mM bistriazene. Reactions were incubated at 37° C. for 42 hours, and analyzed by denaturing polyacrylamide gel electrophoresis (20% gel) followed by autoradiography the gels were intentionally overexposed to better visualize bands corresponding to interstrand crosslinks. Large amounts of unreacted oligonucleotides were also visualized under these conditions.

As shown in FIG. 5, the results obtained with nitrogen mustard and the p-xylyl bistriazene derivative demonstrate that the oligonucleotides were stably covalently crosslinked by both the nitrogen mustard, a known crosslinking agent, as well as by the p-xylyl bistriazene of the instant invention. As can also be seen from FIG. 5, CCNU, a clinically employed DNA interstrand crosslinking agent, was not as effective at forming crosslinks as the p-xylyl bistriazene derivative.

All compounds examined caused extensive DNA strand breakage, because of which labile adducts were not observable.

Plasmid DNA Strandbreaking. DNA strand breaks may occur via the hydrolysis of labile alkylation sites. A single strand break allows the relaxtion of supercoiled DNA to afford a nicked open circular form. Double strand breakage producing linear plasmid DNA occurs upon the hydrolysis of two labile alkylation sites close to one another on opposite DNA strands. These alkylation events may be either an interstrand crosslink, or discrete, but closely located, monoalkylations.

Dialkyltriazenes afford more strand breakage than alkylsulfates and sulfonates. Bistriazenes are approximately 10–200 times more efficacious at producing strand breaks than dialkyltriazenes. Bistriazenes afford significant quantities of linear DNA, whereas simple dialkyltriazenes produce only small amounts of the linear form, and only traces are detectable in the reaction of alkylsulfates with plasmid DNA. Restriction endonuclease treatment of bistriazene-modified DNA suggests that linearization is not highly specific for sequences on the plasmid.

The supercoiled plasmid strand break assay was carried out in a solution of 0.15 ug of pBR322 DNA in 9.5 ul of TE buffer (10 mM) Tris, 0.1, mMEDTA, pH 7.4) prepared at room temperature. A 0.5 ul aliquot of compound in DMSO was added, the solution vortexed lightly, and the samples incubated at 37° for 48 hours. Loading buffer (2 ul, 40% glycerol, and 1% bromphenol blue in TAE buffer) was added to each sample, and a 3 ul aliquot was analyzed by agarose gel electrophoresis (0.9% gel, 1.5 ug ethidium bromide/ml gel), and visualized by fluorescence.

The experimental results shown in FIG. 6 indicate that the bistriazenes examined afford higher levels of DNA modification than do simple dialkyltriazenes such as dimethyltriazene, and that the bistriazenes afford far more linearized DNA, indicated labile alkylation events on opposite strands of the DNA in close proximity to one another. These alkylation events may be a labile interstrand crosslink or discrete alkylation events near one another on opposite strands.

This suggests interaction of the bistriazine with DNA prior to forming active alkylating agent rather than simple hydrolysis to alkyldiazonium ion.

PHARMACEUTICAL PREPARATIONS

The bistriazene compounds of the present invention, or physiologically acceptable salts therof, can be formulated into a pharmaceutical composition comprising an effective anti-cancer amount of the compound and a pharmaceutically acceptable carrier. An effective anti-cancer amount of the pharmaceutical composition will be administered to the subject, human, animal, or mammal, in a manner which inhibits cancer cell growth or replication. The amount of the compound and the specific pharmaceutically acceptable carrier will vary depending upon the host and its condition, the mode of administration, and the type of cancer being treated.

In a particular aspect, the pharmaceutical composition comprises a bistriazene anti-cancer compound in effective unit dosage form. As used herein, the term "effective unit dosage" or "effective unit dose" is denoted to mean a predetermined anti-cancer amount sufficient to be effective against the cancer in vivo. Pharmaceutically acceptable carriers are materials useful for the purpose of administering the medicament, which are preferably non-toxic, and may be liquid materials which are otherwise inert and medically acceptable, and are compatible with the active ingredients. The pharmaceutical compositions may contain other active ingredients such as antimicrobial agents and other agents such as preservatives.

These pharmaceutical compositions may take the form of a solution, an emulsion, suspension, ointment or cream. They may be administered parenterally, orally or topically, as an aerosol, spray, or drops, said parenteral administration being conducted intraperitoneally, intramuscularly, subcutaneously, intravenously, intraarticularly, intraarterially, or transdermally, depending upon whether the preparation is used to treat internal or external cancers.

The compositions may contain the compound in an amount of from about 0.1%—about 99% by weight of the total composition, preferably about 1 to about 90% by weight of the total composition. For parenteral injection, the bistriazene compound can be dissolved in a pharmaceutically suitable carrier such as purified corn oil, propylene glycol, triolene, or dimethyl sulfoxide, and the dose may be about 0.1 mg to about 1000 mg per kilogram per day. If administered intraperitoneally, the compounds may be dissolved in a suitable vehicle, as above, and the dose may be about 1 mg to about 500 mg per kilogram per day. If injected intramuscularly, the compounds can be dissolved in oil or another compatible vehicle, and the dose can be about 0.1 mg to about 1000 mg per kilogram per day. In any case, injections can be carried out once or several times per day over a five day course depending upon the route of administration and the condition of the patient. After such courses, a recovery period of various length may be necessary. Additional courses may then be required under specific conditions. Total adult doses can range from about 0.1 to about 5000 mg, with dosages in the range of from about 10 to about 1000 mg being preferred. For certain particular applications, oral administration of bistriazenes encapsulated in liposomes or time-release formulations or dispersed in compatible emulsions together with stabilizing and/or dispersing agents may be the method of choice.

For topical application, to treat surface lesions such as basal cell and squamous cell carcinomas or non-metastasized melanomas, as well as certain non-malignant conditions which are characterized by rapid cell proliferation but which may not be amenable to surgical treatment, bistriazenes may be formulated in oil or cream.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for treating cancer in a mammal, comprising administering to said mammal an anti-cancer effective amount of a bistriazene compound or a physiologically acceptable salt thereof of the formula:

wherein
the Linker is selected from the group consisting of alkylene, substituted alkylene of chain length 1–20, aralkylene or substituted aralkylene, polycyclic aralkylene, heterocyclic aralkylene, trans-2-butenylene, and 1-4-di-methyl-cyclohexylene wherein the triazine moieties are separated by 1–30 carbon atoms;

EG is identical or independently selected from the group consisting of alkyl, substituted alkyl of chain length 1–20, aralkyl or substituted aralkyl, polycyclic aralkyl, aryl groups and heterocyclic groups of 2–40 non-hydrogen atoms, containing 1–6 rings; and R or R' is identical to EG or to one another, or is independently selected from the group consisting of hydrogen, alkyl, substituted alkyl of chain length 1–20, or aralkyl or substituted aralkyl, polycyclic aralkyl, aryl, and heterocyclic groups of 2–40 non-hydrogen atoms, containing 1–6 rings.

2. The method of claim 1, wherein said bistriazene compound is bis(methyltriazeno)-p-xylene, bis(methyltriazeno)-2-butene, or bis(methyltriazeno)ethane.

3. The method of claim 1, wherein said bistriazene compound is administered in the form of a solution, emulsion, suspension, ointment, or cream.

4. The method of claim 1, wherein said bistriazene compound is administered parenterally, orally, or topically, as an aerosol, spray, or drops, said parenteral administration being conducted intraperitoneally, intramuscularly, subcutaneously, intravenously, intraarterially, intraarticularly or transdermally.

5. The method of claim 4, wherein said bistriazene compound is administered parenterally, dissolved in oil or other pharmceutically acceptable carrier in a dose of from about 0.1 mg to about 1000 mg per kilogram per day.

6. The method of claim 4, wherein said bistriazene compound is administered intraperitoneally, dissolved in a pharmaceutically acceptable carrier, in a dose of from about 1 mg to about 500 mg per kilogram per day.

7. The method of claim 4, wherein said bistriazene compound is administered intramuscularly, dissolved in oil or another compatible vehicle, in a dose of from about 0.1 mg to about 1000 mg per kilogram per day.

8. The method of claim 4, wherein said bistriazene compound is administered orally, encapsulated in liposomes or time-release formulations, or dispersed in compatible emulsions together with stabilizing or dispersing agents.

9. The method of claim 4, wherein said bistriazene compound is administered topically, formulated in an oil or cream.

10. The method of claim 5, 6, 7, 8, or 9, wherein said bistriazene compound is administered once or several times per day over a five day course.

11. A method for treating cancer in a mammal as recited in claim 1, wherein
said Linker is selected from the group consisting of alkylene, trans-2-butenylene, 1,4-di-methyl-cyclohexylene, and aralkylene;

EG is an alkyl group of chain length 1–20; and
R and R' are each hydrogen.

12. A method for treating cancer in a mammal, comprising administering to said mammal an anti-cancer effective amount of a bistriazene compound or a physiologically acceptable salt thereof of the formula:

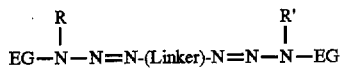

wherein
the Linker is selected from the group consisting of ethylene, butylene, trans-2-butenylene, o-xylylene, p-xylylene and 1-4-di-methyl-cyclohexylene;
EG is methyl; and
R and R' are each hydrogen.

13. A method for treating cancer in a mammal, which comprises administering to said mammal an anti-cancer effective amount of 1,4-bis(methyltriazeno)-trans-2-butene, or a physiologically acceptable salt thereof.

14. The method of claim 1, wherein:
substituted alkylene is an alkylene moiety substituted by a substitutent selected from the group consisting of a radical of an alkyl amine, alkyl ether, thioether, haloalkyl, silane, phosphine, alcohol and amine, substituted aralkylene is an aralkylene moiety substituted by a substitutent selected from the group consisting of a radical of an alkyl amine, alkyl ether, thioether, haloalkyl, silane, phosphine, alcohol and amine, substituted polycyclic aralkylene is a polycylic aralkylene moiety substituted by a substitutent selected from the group consisting of a radical of an alkyl amine, alkyl ether, thioether, haloalkyl, silane, phosphine, alcohol and amine, and substituted heterocyclic aralkylene is a heterocyclic aralkylene moiety substituted by a substitutent selected from the group consisting of a radical of an alkyl amine, alkyl ether, thioether, haloalkyl, silane, phosphine, alcohol and amine.

* * * * *